US006599938B1

(12) United States Patent
Al-Abed et al.

(10) Patent No.: US 6,599,938 B1
(45) Date of Patent: Jul. 29, 2003

(54) COMPOUNDS HAVING MIF ANTAGONIST ACTIVITY

(75) Inventors: Yousef Al-Abed, Locust Valley, NY (US); Richard J. Bucala, Cos Cob, CT (US)

(73) Assignee: The Picower Institute of Medical Research, Manhasset, NY (US)

( * ) Notice: Subject to any disclaimer, the term of this patent is extended or adjusted under 35 U.S.C. 154(b) by 0 days.

(21) Appl. No.: 09/699,258

(22) Filed: Oct. 27, 2000

Related U.S. Application Data

(60) Provisional application No. 60/162,467, filed on Oct. 29, 1999.

(51) Int. Cl.[7] ...................... A61K 31/24; A61K 31/195; C07C 323/00; C07C 229/00; C07C 251/00
(52) U.S. Cl. .................... 514/538; 514/539; 514/567; 560/9; 560/35; 560/104; 562/426; 562/440; 562/495
(58) Field of Search ................................. 562/426, 440, 562/495; 560/9, 35, 104; 514/538, 539, 567

(56) References Cited

U.S. PATENT DOCUMENTS 4,204,071 A  *  5/1980  Anderson et al.
4,401,820 A  *  8/1983  Chibata et al.

OTHER PUBLICATIONS

Barco et al, A One–pot Synthesis of Nitrohydroxylated Pyrrolidine and Piperidine Ring Systems by Tandem Michale–Henry Reaction, 1994, Tetrahedron Letters, 35(49), pp. 9293–9296.*
Mar., 1977, Advanced Organic Chemistry, 2nd edition, McGraw–Hill Book Company, New York, pp. 806–807.*
Islam et al Journal of the Bangladesh Chemical Society 1994, 7(2) pp. 186–90. Abstract only.*
Islam et al Journal of the Bangladesh Chemical Society 1998, 7(1+2) pp. 9–13. Abstract only.*
Baggaley et al European Journal of Medicinal Chemistry 1988, 23(6) pp. 523–531. Abstract only.*
Bloom, B.R., et al., "Mechanism of a Reaction in Vitro Associated with Delayed–Type Hypersensitivity", Science, vol. 153, pp. 80–82 (1966).
David J.R. "Delayed Hypersensitivity In Vitro: Its Mediation by Cell–Free Substances Formed By Lymphoid Cell–Antigen Interaction", Proc. Natl. Acad. Sci. USA, Vol. 56, pp. 72–77 (1966).
Weiser, W.Y., et al., et al., "Studies on Human Migration Inhibitory Factor: Characterization of Three Molecular Species", The Journal of Immunology, vol. 126, No. 5, pp. 1958–1962 (1981).

(List continued on next page.)

Primary Examiner—Johann Richter
Assistant Examiner—Paul A. Zucker
(74) Attorney, Agent, or Firm—Piper Rudnick LLP; Steven B. Kelber

(57) ABSTRACT

There is disclosed a genus of optionally substituted Schiff base condensation products (and the carba analogs thereof) comprising an amino acid component and a benzaldehyde component, that have MIF (macrophage migration inhibitory factor) antagonist activity. The compounds are useful for treating a variety of diseases involving inflammatory activity or pro-inflammatory cytokine responses, such as autoimmune diseases, asthma, arthritis, EAE, ARDS and various forms of sepsis and septic shock, and other conditions characterized by underlying MIF responses including, for instance, tumor growth and neovascularization.

15 Claims, 2 Drawing Sheets

OTHER PUBLICATIONS

Nathan, C.F., et al., "Characterization of a Lymphocyte Factor Which Alters Macrophage Functions", The Journal of Experimental Medicine, vol. 137, No. 4, pp. 275–290 (1973). (erroneously cited in specification as pp. 275–288).

Nathan, C.F., et al., "Alterations of Macrophage Functions by Mediators From Lymphocytes", The Journal of Experimental Medicine, vol. 133, pp. 1356–1376 (1971).

Churchill, W.H., et al., "Macrophages Activated as Suspension Cultures with Lymphocyte Mediators Devoid of Antigen Become Cytotoxic for Tumor Cells", The Journal of Immunology, vol. 115, No. 3, pp. 781–786 (1975).

McInnes, A., et al., "Interleukin 4 Induces Cultured Monocytes/Macrophages to Form Giant Multinucleated Cells", J. Exp. Med., vol. 167, pp. 598–611 (1988).

Thurman, G.B., et al., "MIF–Like Activity of Natural and Recombinant Human Interferon–γ and Their Neutralization by Monoclonal Antibody", The Journal of Immunology, vol. 134, No. 1, pp. 305–309 (1985).

Weiser, W.Y., et al., "Molecular Cloning of a cDNA Encoding a Human Macrophage Migration Inhibitory Factor", Proc. Natl. Acad. Sci. USA, vol. 86, pp. 7522–7526 (1989).

Weiser, W.Y., et al., "Human Recombinant Migration Inhibitory Factor Activates Human Macrophages to Kill *Leishmania donovani*", The Journal of Immunology, vol. 147, No. 6, pp. 2006–2011 (1991).

Pozzie, L.M., et al., "Human Recombiant Migration Inhibitory Factor Activates Human Macrophages to Kill Tumor Cells", Cellular Immunology, vol. 145, pp. 372–379 (1992).

Weiser, W.Y., et al., "Recombinant Human Migration Inhibitory Factor has Adjuvant Activity", Proc. Natl. Acad. USA, vol. 89, pp. 8049–8052 (1992).

Cunha, F.Q., et al., "Recombinant Migration Inhibitory Factor Induces Nitric Oxide Synthase in Murine Macrophages", The Journal of Immunology, vol. 150, No. 5, pp. 1908–1912 (1993).

Bucala, R., "MIF Rediscovered: Cytokine, Pituitary Hormone, and Glucocorticoid–Induced Regulator of the Immune Response", The FASEB Journal vol. 10, pp. 1607–1613 (1996).

Rice, G.C., et al., "Chapter 24, Macrophage Migration Inhibitory Factor (MIF): A Critical Upstream Regulator of Acute and Chronic Inflammatory Responses", Annual Reports in Medicinal Chemistry, vol. 33, pp. 243–252 (1998).

Donnelly, S.C., et al., "Macrophage Migration Inhibitory Factor: A Regulator of Glucocorticoid Activity with a Critical Role in Inflammatory Disease", Molecular Medicine Today, vol. 3, pp. 502–507 (1997).

Chesney, J., et al., "An Essential Role for Macrophage Migration Inhibitory Factor (MIF) in Angiogenesis and the Growth of a Murine Lymphoma", Molecular Medicine, vol. 5, pp. 181–191 (1991).

Rosengren, E., et al., "The Immunoregulatory Mediator Macrophage Migration Inhibitory Factor (MIF) Catalyzes a Tautomerization Reaction", Molecular Medicine, vol. 2, No. 1, pp. 143–149 (1996).

Bendrat, K., et al., "Biochemical and Mutational Investigations of the Enzymatic Activity of Macrophage Migration Inhibitory Factor", Biochemistry, vol. 36, pp. 15356–15362 (1997).

Fingl, E., et al., "General Principles", Chapter 1, The Pharmacological Basis of Therapeutics, Fifth Edition, p. 1–53 (1975).

Olah, G.A., et al., "Preparation of α–Bromo– and α–Chlorocarboxylic Acids from α–Amino Acids", Helvetica Chimica Acta, vol. 66, Fasc. 4, Nr. 101, pp. 1028–1030 (1983). (erronesously cited in specification as "Chimica Acta")

Cushman, D.W., et al., "Design of Potent Competitive Inhibitors of Angiotensin–Converting Enzyme. Carboxyalkanoyl and Mercaptoalkanoyl Amino Acids", Biochemistry, vol. 16, No. 25, pp. 5484–5491 (1977).

Sonogashira, K., et al., "A Convenient Synthesis of Acetylenes: Catalytic Substitutions of Acetylenic Hydrogen with Bromoalkenes, Iodoarenes, and Bromopyridines", Tetrahedron Letters, vol. 16, No. 50, pp. 4467–4470 (1975).

Tischler, A.N., et al., "6–Substituted Indoles from 0–Halonitrobenzenes", Tetrahedron Letters, vol. 27, No. 15, pp. 1653–1656 (1986).

Denmark, S.E., et al., "(E)–3–(Trimethylsilyl)–2–propen–1–ol. An Improved Preparation", J. Org. Chem., vol. 47, pp. 4595–4597 (1982). (Erronesously cited in specification as "Organic Chemistry").

Brandsma, L. et al., "Reduction of Acetylenic Compound to (E)–Olefins by Alkali Metals—An Investigation of the Scope", Eur. J. Org. Chem., vol. 4; pp. 775–779 (1999). (erronesously cited in specification as "Lambert").

Schreiber, S.L., et al., "Reactions that Proceed with a Combination of Enantiotopic Group and Diastereotopic Face Selectivity Can Deliver Products with Very High Enanthiomeric Excess: Experimental Support of a Mathematical Model", J. Amer. Chem. Soc., vol. 109, pp. 1525–1529 (1987).

Jung, M. J., et al., "Mechanism of the Stereospecific Irreversible Inhibition of Bacterial Glutamic Acid Decarboxylase by (R)–(–)–4–Aminohex–5–ynoic Acid, an Analogue of 4–Aminobutyric Acid", Biochemstry, vol. 17, pp. 2628–2632 (1978).

Database USPATFULL on STN (Columbus, OH, USA), No. 131:271690, Synthesis of 2',5'–dihydropyrrolo[3',4':1,2][60] fullerene derivatives, Wu, et al., May 1999 *abstract*.

* cited by examiner

COMPOUNDS HAVING MIF ANTAGONIST ACTIVITY

CROSS REFERENCE TO RELATED APPLICATIONS

This application claims the benefit of U.S. Provisional Application No. 60/162,467, filed Oct. 29, 1999, hereby incorporated by reference.

TECHNICAL FIELD OF THE INVENTION

The present invention provides a genus of optionally substituted Schiff base condensation products (and the carba analogs thereof) comprising an amino acid component and a benzaldehyde component, that have MIF (macrophage migration inhibitory factor) antagonist activity. Specifically, the compounds are useful for treating a variety of diseases involving inflammatory activity or pro-inflammatory cytokine responses, such as autoimmune diseases, asthma, arthritis, EAE, ARDS and various forms of sepsis and septic shock, and other conditions characterized by underlying MIF responses including, for instance, tumor growth and neovascularization.

BACKGROUND OF THE INVENTION

Human MIF was first cloned in 1989 and its activity has been investigated in a number of studies. MIF was the first lymphokine to be discovered and was originally identified by its ability to prevent the migration of guinea pig macrophages in vitro (Bloom & Bennett, *Science* 153:80–82, 1966; David, *Proc. Natl. Acad. Sci. USA* 56:72–77, 1966). Given this activity, the role of MIF activity in inflammation and the immune system was investigated, however the precise role of MIF in either local or systemic inflammatory responses remained largely undefined in the course of this early work. Likewise the role of MIF in other physiological and pathophysiological is still being defined.

MIF was reported to be associated with delayed-type hypersensitivity reactions (Bloom & Bennett, 1966, supra; David, 1966, supra), to be produced by lectin-activated T-cells (Weiser et al., *J. Immunol.* 126:1958–1962, 1981), and to enhance macrophage adherence, phagocytosis and tumoricidal activity (Nathan et al., *J. Exp. Med.* 137:275–288, 1973; Nathan et al., *J. Exp. Med.* 133:1356–1376, 1971; Churchill et al., *J. Immunol.* 115:781–785, 1975). Unfortunately, many of these early studies used mixed culture supernatants that were shown later to contain other cytokines, such as IFN-γ and IL-4, that also have macrophage migration inhibitory activity (McInnes & Rennick, *J. Exp. Med.* 167:598–611, 1988; Thurman et al., *J. Immunol.* 134:305–309, 1985).

Recombinant human MIF was originally cloned from a human T cell library (Weiser et al., *Proc. Natl. Acad. Sci. USA* 86: 7522–7526, 1989), and was shown to activate blood-derived macrophages to kill intracellular parasites and tumor cells in vitro, to stimulate IL-1β and TNFα expression, and to induce nitric oxide synthesis (Weiser et al., *J. Immunol.* 147:2006–2011, 1991; Pozzi et al., *Cellular Immunol.* 145:372–379, 1992; Weiser et al., *Proc. Natl. Acad. Sci. USA* 89:8049–8052, 1992; Cunha et al., *J. Immunol.* 150:1908–1912, 1993). While the conclusions available from several of these early reports are confounded by the presence of a bioactive mitogenic contaminant in the recombinant MIF preparations used, the potent pro-inflammatory activities of MIF have been confirmed in other studies that do not suffer from this complicating factor (reviewed in Bucala, *The FASEB Journal* 10:1607–1613, 1996). More recent MIF studies have capitalized on the production of recombinant MIF in purified form as well as the development of MIF-specific polyclonal and monoclonal antibodies to establish the biological role of MIF in a variety of normal homeostatic and pathophysiological settings (reviewed, for instance, in Rice et al., *Annual Reports in Medicinal Chemistry* 33:243–252, 1998). Among the most important insights of these later reports following the "re-discovery" of MIF has been the recognition that MIF not only is a cytokine product of the immune system, but also is a hormone-like product of the endocrine system, particularly the pituitary gland. Moreover, this recent work has underscored the potent activity of MIF as a counter-regulator of the anti-inflammatory effects of the glucocorticoids (both those endogenously released and those therapeutically administered), with the effect that the normal activities of glucocorticoids to limit and suppress the severity of inflammatory responses are inhibited by MIF, such that the endogenous MIF response is seen as a cause or an exacerbative factor in a variety of inflammatory diseases and conditions (reviewed in Donnelly and Bucala, *Molecular Medicine Today* 3:502–507, 1997). MIF has also been linked to tumor growth and neovascularization (angiogenesis), suggesting a further need for MIF antagonists in the area of oncology and cancer treatment (Chesney et al., *Molecular Medicine* 5:181–191, 1999).

This experimental work underscores the need for inhibitors of MIF, and MIF antagonists have been identified and shown to have a variety of therapeutic activities, including activity for multiple inflammatory diseases, cytokine-mediated toxicities, asthma, and autoimmune diseases (e.g., rheumatoid arthritis, graft versus host disease, insulin-dependent diabetes, and various forms of lupus). These MIF antagonist agents, however, have been "biological" agents that are designed to bind MIF (e.g., antibody) and to prevent its expression (e.g., antisense oligonucleotide). Such biological agents, unfortunately, have certain limitations with regard to their clinical utility. Therefore, there is a need in the art to discover and develop small organic molecules that function as MIF antagonists and further posses the benefits of small organic molecule therapeutics versus larger, polymeric protein and nucleic acid-based-based therapeutic agents.

SUMMARY OF THE INVENTION

The present invention provides a compound of Formula I:

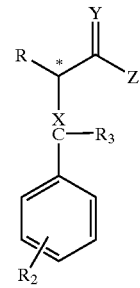

wherein X is nitrogen or carbon;
wherein Y is O, C(R$_1$)$_2$, or S;
wherein Z is OH, R$_1$, —CH$_2$—N(R$_1$)$_2$, or SR$_1$;
wherein R$_1$ is independently H, straight or branched C$_1$–C$_6$ alkyl, straight or branched C$_2$–C$_6$ alkenyl, or if R$_1$ is attached to carbon (but not if R$_1$ is attached to N or S), straight or branched C$_1$–C$_6$ alkoxy;

wherein $R_2$ is a single or multiple substitution independently H, OH, $R_1$, $N(R_1)_2$, $SR_1$ or a halogen;

wherein $R_3$ is absent, H, $R_1$, or a halogen;

wherein * and C mark potentially asymmetric carbon atoms and, in each instance of R, X, Y, Z, $R_1$, and $R_3$ where * or C or both are asymmetric, all diastereomers are included in Formula I;

wherein R is the side-chain of any naturally occurring alpha amino acid such that R together with X, Y and Z comprise, when Y is O and Z is OH, an aromatic, aliphatic or heterocyclic D or L alpha amino acid moiety linked as a Schiff base or a reduced Schiff base (if X is N) or as a carba analog thereof (if X is C) to an optionally substituted benzaldehyde moiety, and wherein if Y is other than O, or Z is other than OH, R together with X, Y and Z comprise a substituted amino acid moiety, an analog of an amino acid moiety or a protected amino acid moiety;

and pharmaceutically acceptable salts thereof.

Preferably, X is N, Y is O, and Z is OMe such that together with R they form a protected L aliphatic or aromatic amino acid moiety. Preferably, $R_2$ is OH, and $R_3$ is H. Even more preferably $R_2$ is in a para position to comprise a para-hydroxybenzaldehyde moiety.

A preferred subset of these preferred compounds is described by Formula II, wherein R is H (compound 1); wherein R is —$CH_3$ (compound 2 or compound 2a corresponding to L alanine and compound 2b corresponding to D alanine); wherein R is —$CH(CH_3)_2$ (compound 3); wherein R is —$CH_2CH(CH_3)_2$ (compound 4); wherein R is —CH($CH_3$)$CH_2CH_3$ (compound 5); wherein R is —$CH_2CH_2SCH_3$ (compound 6); and wherein R is —$CH_2OH$ (compound 7). Formula II:

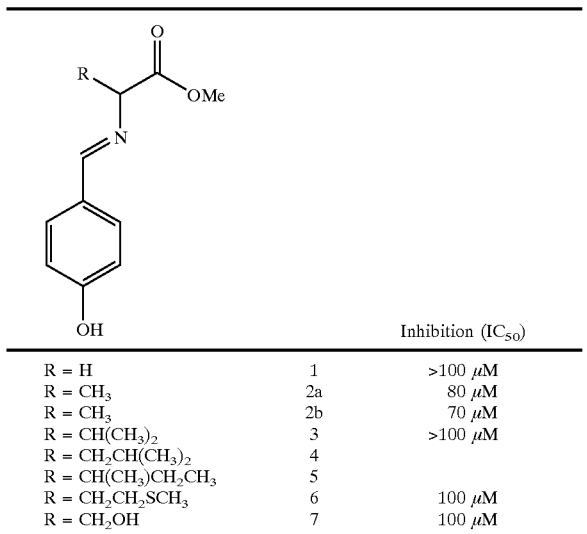

| | | Inhibition ($IC_{50}$) |
|---|---|---|
| R = H | 1 | >100 μM |
| R = $CH_3$ | 2a | 80 μM |
| R = $CH_3$ | 2b | 70 μM |
| R = $CH(CH_3)_2$ | 3 | >100 μM |
| R = $CH_2CH(CH_3)_2$ | 4 | |
| R = $CH(CH_3)CH_2CH_3$ | 5 | |
| R = $CH_2CH_2SCH_3$ | 6 | 100 μM |
| R = $CH_2OH$ | 7 | 100 μM |

Still more preferred, R is the side-chain of a naturally-occurring aromatic alpha amino acid, X is N, Y is O, and Z is OMe such that together with R they form a protected L aromatic amino acid moiety. Most preferably, $R_2$ is OH, and $R_3$ is H. Most preferably, $R_2$ is in a para position to comprise a para-hydroxybenzaldehyde moiety product. Most preferably, R is —$CH_2$-phenyl (compound 8), or R is —$CH_2$-para-hydroxyphenyl (compound 9), or R is —$CH_2$-indoyl (compound 10).

The invention further provides a pharmaceutical composition comprising a compound of Formula I, as a pharmaceutically acceptable salt thereof, together with a pharmaceutically acceptable carrier or diluent.

The invention further provides a compound of formula I, or a pharmaceutically acceptable salt thereof, as a pharmaceutical composition comprising either of the aforesaid, for use in a medicine or for the manufacture of a medicament for the treatment or prevention of cancer or of inflammatory disorders including arthritis, proliferative vascular disease, ARDS (acute respiratory distress syndrome), cytokine-mediated toxicity, sepsis, septic shock, psoriasis, interleukin-2 toxicity, asthma and MIF-mediated conditions. The present invention further provides a method for treating or preventing cancer, arthritis, proliferative vascular disease, ARDS (acute respiratory distress syndrome), cytokine-mediated toxicity, sepsis, septic shock, psoriasis, interleukin-2 toxicity, asthma, MIF-mediated conditions, autoimmune disorders including rheumatoid arthritis, insulin-dependent diabetes, multiple sclerosis, graft versus host disease, lupus syndromes, or any condition characterized by local or systemic MIF release or synthesis.

In accordance with the activity of MIF to interfere with the anti-inflammatory effects of steroids (such as the anti-inflammatory glucocorticoids), the compounds of Formula I find further utility to enhance the activity and therapeutic benefits of both endogenously arising and exogenously administered steroidal anti-inflammatory agents. Such benefits may, in some cases, be most evident by a reduced need for steroid therapy (e.g., lower dose amount or frequency; less potent agent; reduced need for systemic administration) or by reduced side-effects associated with steroid administration. The benefits of administering an MIF antagonist agent (and specifically a compound of Formula I) may be realized as a monotherapy, using only the MIF antagonist agent of the present invention, or as a combination therapy with additional anti-inflammatory agents, including especially, but without limitation, an anti-inflammatory steroid. Such combination therapy may be achieved through administration of a single formulation or pharmaceutical composition that combines the MIF antagonist agent (particularly an agent of Formula I) with at least one other anti-inflammatory agent (which may be a steroidal or a non-steroidal anti-inflammatory agent), or through administration of separate formulations or pharmaceutical compositions in conjunction with each other (e.g., one composition comprising the MIF antagonist agent of Formula I, and at least one other composition comprising at least one steroidal or non-steroidal anti-inflammatory agent), or both.

BRIEF DESCRIPTION OF THE DRAWINGS

FIG. 1 provides a comparison of the activity of an anti-MIF monoclonal antibody (100 μg/ml) vs L-tryptophan/para-hydroxybenzaldehyde Schiff base (compound 10; 10 μM) vs D-tryptophan/para-hydroxybenzaldehyde Schiff base (compound 10b; 10 μM) to inhibit serum-induced cell proliferation in assay populations of quiescent NIH/3T3 fibroblasts. The proliferation effect depends on MIF bioactivity, such that neutralization of MIF is reflected in an inhibition of proliferation, and this inhibitory effect is predictive of clinical utility of the active MIF antagonist agent.

DETAILED DESCRIPTION OF THE INVENTION

Figure 1:
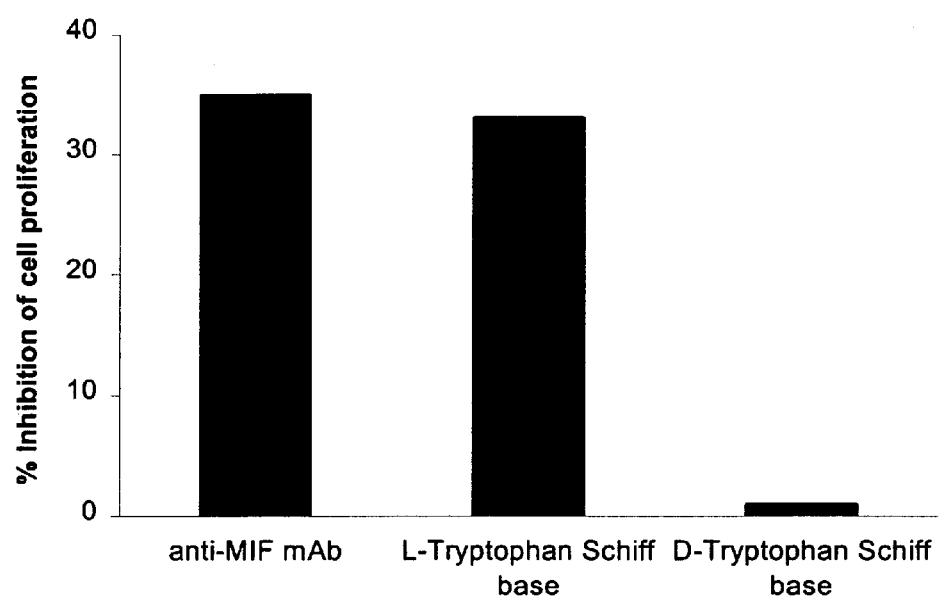
FIG. 1 shows that MIF antagonist agents of the present invention can suppress serum-induced cell proliferation to a degree equal to the suppressing activity of a neutralizing anti-MIF monoclonal antibody.

MIF was found to catalyze a tautomerization reaction (Rosengren, et al., *Molecular Medicine* 2:143–149, 1996), and although the most active substrate identified to date is the non-physiological D-isomer of dopachrome, the observation that MIF can catalyze a tautomerization reaction points to the possibility of developing inhibitors of MIF enzymatic activities as therapeutic MIF antagonists (see U.S patent application Ser. No. 08/602,929, filed Feb. 16, 1996, the disclosure of which is incorporated by reference herein).

According to the present invention, unless otherwise indicated, alkyl groups having three or more carbon atoms may be straight or branched chain. In addition, alkenyl or alkynyl groups having four or more carbon atoms, or alkoxy groups having three carbon atoms, may be straight or branched chain. The compounds of formula I may contain one or more asymmetric centers and can exist as alternative tautomer forms or diastereoisomers. The present invention includes both mixtures and separate individual isomers and tautomers, although, structure-activity data indicates that for some compounds of the inventive genus, one enantiomer has more therapeutic activity than the other.

A class of compounds has been synthesized and further characterized as to the chemical nature of the amino acid moiety. Compounds of one subset are Schiff bases comprising a protected aliphatic amino acid. These include compounds 1–7.

| | | Inhibition (IC$_{50}$) |
|---|---|---|
| R = H | 1 | >100 μM |
| R = CH$_3$ | 2a | 80 μM |
| R = CH$_3$ | 2b | 70 μM |
| R = CH(CH$_3$)$_2$ | 3 | >100 μM |
| R = CH$_2$CH(CH$_3$)$_2$ | 4 | |
| R = CH(CH$_3$)CH$_2$CH$_3$ | 5 | |
| R = CH$_2$CH$_2$SCH$_3$ | 6 | 100 μM |
| R = CH$_2$OH | 7 | 100 μM |

The present invention encompasses compounds and the use of compounds that are identified as MIF antagonists by their inhibition of an in vitro enzymatic assay in which MIF catalyzes the tautomerization of a dopachrome-related MIF substrate to a colorless product. This assay for inhibition of MIF tautomerase activity is predictive of clinical utility as an MIF antagonist therapeutic agent. In the table above (describing compounds 1–7 according to Formula II), an IC$_{50}$ value was obtained for compounds 1–3 and 6–7, as shown in the table, in such an MIF tautomerase assay. Unless specifically indicated to the contrary, references made herein to an inhibitory concentration (e.g., IC$_{50}$ or other activity index) refer to the inhibitory activity of a test compound in an MIF tautomerase assay (as further described in detail, for instance, in Bendrat et al., *Biochemistry* 36:15356–15362, 1997).

The general method of performing an assay for MIF dopachrome tautomerase activity begins with the preparation and oxidation of a DOPA-related substrate precursor, such as L-3,4-dihydroxyphenylalanine methyl ester. This oxidation, typically with sodium periodate, generates the corresponding dopachrome derivative (e.g., L-3,5-dihydro-6-hydroxy-5-oxo-2H-indole-2-carboxylic acid methyl ester), which is typically orange-colored and comprises a convenient substrate for use in a photometric assay for the activity of MIF as a tautomerase. Upon addition of MIF (typically a purified preparation of recombinant MIF at a final concentration of 50–1000 ng/ml), the tautomerization of the colored dopachrome substrate to (in this example) a colorless 5,6-dihydroxyindole-2-caboxylic acid methyl ester product occurs. The enzymatic activity of MIF is measured as the rate of de-colorization of the colored solution of the dopachrome-related substrate in a suitable buffer, typically monitored at 475 nm (or 550 nm for substrate concentrations in excess 0.5 nM). A test compound may be included in the assay solution such that the effect of the test compound on MIF tautomerase activity (i.e., as an inhibitor) may be measured by noting the change in kinetics compared to control assays performed in the absence of the test inhibitorcompound. In particular, the MIF tautomerase assay may be conducted essentially as follows:

L-3,4-dihydroxyphenylalanine methyl ester (e.g., Sigma D-1507), the dopachrome substrate precursor, is prepared as a 4 mM solution in dd $H_2O$. Sodium periodate is prepared as an 8 mM solution in dd$H_2O$. Assay Buffer (50 mM potassium phosphate/1 mM EDTA, pH 6.0) is prepared. Purified recombinant MIF is prepared in 150 mM NaCl/20 mM Tris buffer (pH 7.4) as a stock solution convenient to supply MIF at a final concentration of about 700 ng/ml. Immediately prior to initiating the assay, 3.6 ml dopachrome substrate precursor solution, 2.4 ml periodate solution and 4.0 ml Assay Buffer are combined into a homogeneous mixture (this preparation of dopachrome substrate is suitable for assay use after 1 min and for about 30 min thereafter). Test compound (typically prepared as a concentrated stock in DMSO) and MIF are then combined with 0.7 ml Assay Buffer plus 0.3 ml dopachrome substrate solution to provide the desired final concentration of the test compound in a homogeneous mixture, and the optical density of this assay mixture is monitored at 475 nm. Typically, $OD_{475}$ is recorded every 5 sec for 0–60 sec, and the $OD_{475}$ for a given time point is compared to parallel assays where MIF is not added or the test compound is omitted. Inhibition of MIF tautomerase activity by the test compounds is determined by inhibition of the de-colorization of the assay mixture, typically at the 20 sec time point. $IC_{50}$ values for compounds with MIF tautomerase inhibitory activity, corresponding to the concentration of inhibitor that would inhibit MIF tautomerase activity by 50%, are determined by interpolation of the results from MIF tautomerase assays at several different inhibitor concentrations. These $IC_{50}$ values are taken as a useful predictor of the clinical MIF inhibitory activity of the test compounds.

A second exemplary subset of preferred compounds is compounds 8–10 (below), that are Schiff bases of protected L aromatic amino acids. Compound 10 exhibited the most potent MIF antagonist activity with an $IC_{50}$ of 5 μM, while compound 9 had 10 μM $IC_{50}$ and compound 8 showed an $IC_{50}$ of 50 μM in the aforementioned tautomerase assay.

Two corresponding structures made from D aromatic amino acids to produce the S enantiomers are compounds 8b and 10b and they show significantly less MIF antagonist activity.

| | 8b | 10b |
|---|---|---|
| $IC_{50}$ | 100 μM | 90 μM |

Compounds 11–13 are reduced products of the aromatic R enantiomers of the amino acid/para-hydroxy- benzyaldehyde Schiff base compounds 8, 9 and 10, as illustrated below (where "N.A." indicates that the compound was not active as an inhibitor of MIF tautomerase activity at concentrations up to 100 μM).

| | 8 | 9 | 10 |
|---|---|---|---|
| $IC_{50}$ | 50 μM | 10 μM | 5 μM |

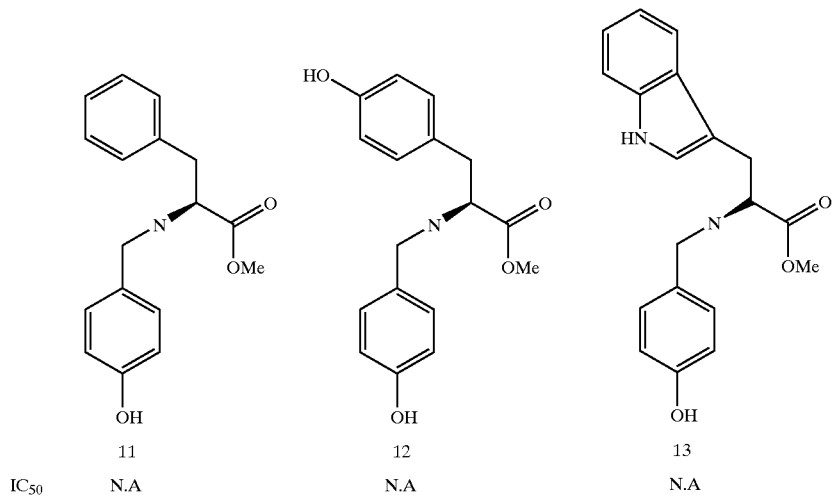

| | 11 | 12 | 13 |
|---|---|---|---|
| IC$_{50}$ | N.A | N.A | N.A |

A further subset of compounds (compounds 14–16) is the condensation products of a protected aromatic amino acid with benzaldehyde.

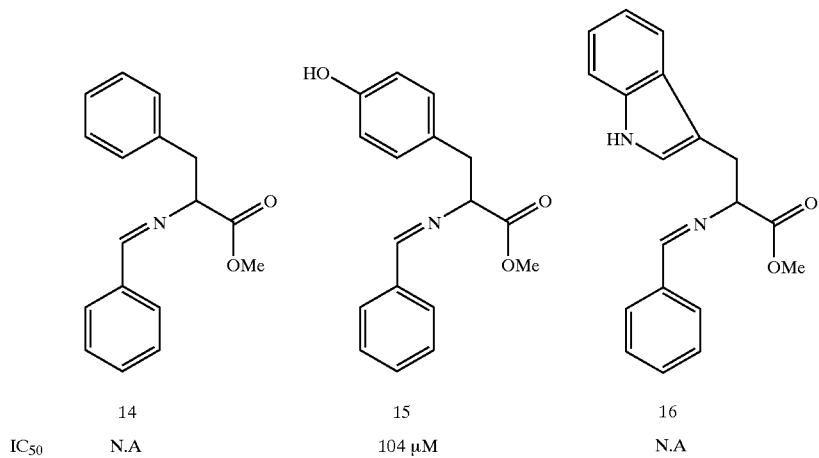

| | 14 | 15 | 16 |
|---|---|---|---|
| IC$_{50}$ | N.A | 104 µM | N.A |

Additional substituted Schiff base compounds are illustrated below as compounds 17–21.

of the benzaldehyde moiety, while the amino acid moiety corresponds to the methyl ester of L tyrosine.

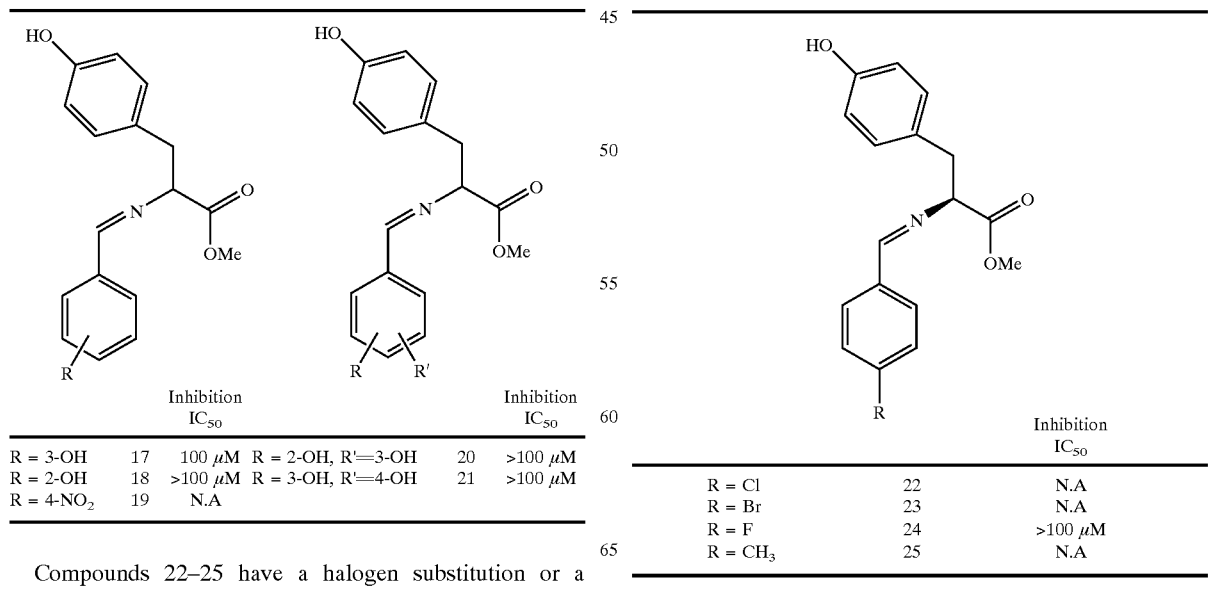

| | | Inhibition IC$_{50}$ | | | Inhibition IC$_{50}$ |
|---|---|---|---|---|---|
| R = 3-OH | 17 | 100 µM | R = 2-OH, R'=3-OH | 20 | >100 µM |
| R = 2-OH | 18 | >100 µM | R = 3-OH, R'=4-OH | 21 | >100 µM |
| R = 4-NO$_2$ | 19 | N.A | | | |

Compounds 22–25 have a halogen substitution or a methyl substitution (instead of hydroxyl) at the para position

| | | Inhibition IC$_{50}$ |
|---|---|---|
| R = Cl | 22 | N.A |
| R = Br | 23 | N.A |
| R = F | 24 | >100 µM |
| R = CH$_3$ | 25 | N.A |

Compound 26, wherein Z is O-tertbutyl, X is N, R is the side chain of tyrosine, Y is O, $R_2$ is para-hydroxy, $R_3$ is H and R, X and Y together comprise a protected aromatic amino acid moiety, is shown below, together with the inhibitory value determined for this compound when present at a concentration of 100 μM in the MIF tautomerase assay.

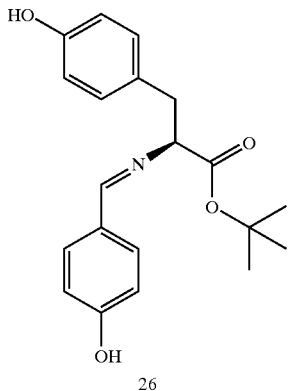

26

% Inhibition = 70%

Compounds 27–29 (see below) comprise a protected L-Trp amino acid moiety together with a benzaldehyde moiety substituted with a halogen in the para position.

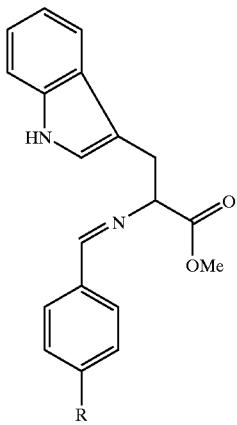

|  |  | Inhibition $IC_{50}$ |
|---|---|---|
| R = Cl | 27 | N.A |
| R = Br | 28 | N.A |
| R = F | 29 | >100 μM |

Pharmaceutical Formulations

The compounds of the present invention have utility in pharmacological compositions for the treatment and prevention of many diseases and disorders characterized by an MIF response, whereby MIF is released from cellular sources and MIF production is enhanced. A compound of the invention can be administered to a human patient by itself or in pharmaceutical compositions where it is mixed with suitable carriers or excipients at doses to treat or ameliorate various conditions characterized by MIF release. A therapeutically effective dose further refers to that amount of the compound sufficient to inhibit MIF tautomerase activity and MIF bioactivity, it being understood that such inhibition may occur at different concentrations such that a person skilled in the art could determine the required dosage of compound to inhibit the target MIF activity. Therapeutically effective doses may be administered alone or as adjunctive therapy in combination with other treatments for tumor growth or associated diseases. Techniques for the formulation and administration of the compounds of the instant application may be found in "Remington's Pharmaceutical Sciences" Mack Publishing Co., Easton, Pa., latest addition.

Suitable routes of administration may, for example, include topical, cutaneous, oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation. In an embodiment, topical administration utilizes excipients such as creams, emulsifiers, and oils. Further embodiments, topical administration utilizes dermal absorption enhancers selected from the group consisting of dimethyl sulfoxide, menthol, lauryl alcohol, lauric acid, arachidonic acid and $C_{10}$–$C_{20}$ polyhydroxy acids and thymol.

Furthermore, one may administer a compound of the present invention in a targeted drug delivery system, for example in a liposome.

The pharmaceutical compositions and compounds of the present invention may be manufactured in a manner that is itself known, e.g., by means of conventional mixing, dissolving, dragee-making, levitating, emulsifying, encapsulating, entrapping, or lyophilizing processes. Pharmaceutical compositions for use in accordance with the present invention thus may be formulated in conventional manner using one or more physiologically acceptable carriers comprising excipients and auxiliaries that facilitate processing of the active compounds into preparations, which can be used pharmaceutically. Proper formulation is dependent upon the route of administration chosen.

For injection, the compounds of the invention may be formulated in aqueous solutions, preferably in physiologically compatible buffers, such as Hank's solution, Ringer's solution, or physiological saline buffer. For transmucosal administration, penetrants appropriate to the barrier to be permeated are used in the formulation. Such penetrants are known in the art.

For oral administration, the compounds can be formulated readily by combining the active compounds with pharmaceutically acceptable carriers well known to those in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the compound with a solid excipient, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various forms of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention identified as neutralizers of MIF activity may be provided as salts with pharmaceutically compatible counterions. Pharmaceutically compatible salts may be formed with many acids, including but not limited to hydrochloric, sulfuric, acetic, lactic, tartaric, malic, succinic, etc.; or bases. Salts tend to be more soluble in aqueous or other protonic solvents than are the corresponding free base forms. Examples of pharmaceutically acceptable salts, carriers or excipients are well known to those skilled in the art and can be found, for example, in *Remington's Pharmaceutical Sciences,* 18th Edition, A. R. Gennaro, Ed., Mack Publishing Co., Easton, Pa., 1990. Such salts include, but are not limited to, sodium, potassium, lithium, calcium, magnesium, iron, zinc, hydrochloride, hydrobromide, hydroiodide, acetate, citrate, tartrate and malate salts, and the like.

Pharmaceutical compositions suitable for use in the present invention include compositions wherein the active ingredients are contained in an effective amount to achieve their intended purpose. More specifically, a therapeutically effective amount means an amount effective to prevent or inhibit development or progression of a disease characterized by MIF release and production in the subject being treated. Determination of the effective amounts is well within the capability of those skilled in the art, especially in light of the detailed disclosure provided herein.

For any compound used in the method of the invention, the therapeutically effective dose can be estimated initially from tautomerase inhibition assays and cell culture assays. Such information can be used to more accurately determine useful doses in humans.

A therapeutically effective dose refers to that amount of the compound that results in a reduction in the development or severity of a disease characterized by MIF release and production. Toxicity and therapeutic efficacy of such compounds can be determined by standard pharmaceutical, pharmacological, and toxicological procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from cell culture assays or animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in *"The Pharmacological Basis of Therapeutics"*, Ch. 1 p. 1).

Dosage amount and interval may be adjusted individually to provide plasma levels of the active moiety which are sufficient to maintain the desired modulating effects, or minimal effective concentration (MEC). The MEC will vary for each compound but can be estimated from in vitro data; e.g., the concentration necessary to achieve a 50–90% inhibition of MIF activity. Dosages necessary to achieve the MEC will depend on individual characteristics and route of administration. However, HPLC assays, bioassays or immunoassays can be used to determine plasma concentrations.

Dosage intervals can also be determined using the MEC value. Compounds should be administered using a regimen that maintains plasma levels above the MEC for 10–90% of the time, preferably between 30–90% and most preferably between 50–90%.

In cases of local administration, such as topical or cutaneous administration, or for instance, direct introduction into a target organ or tissue, or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

Synthesis

In the examples of the syntheses that follow, all reagents and solvents used were purchased at the highest commercial quality. All solvents used were HPLC grade from Fisher. $^1$H (270 MHz) and $^{13}$CNMR (67.5 MHz) NMR spectra were recorded on a JEOL eclipse 270 spectrometer. Coupling constants were reported in Hertz (Hz), and chemical shifts were reported in parts per million (ppm) relative to tetramethylsilane (TMS, 0.0 ppm) with $CDCl_3$, DMSO or $CD_3OD$ as solvent. Thin layer (TLC) and flash column chromatography were performed using Alumina B, F-254 TLC plates form Selecto Scientific and Fisher Scientific Basic alumina Brockman activity I, respectively. The reactions were monitored by TLC and $^1$HNMR and were stopped when the yield of the crude according to $^1$HNMR was 90–95%.

EXAMPLE 1

This example illustrates the synthesis of Schiff base compounds having aliphatic amino acids. To a suspension of anhydrous $MgSO_4$ in $CH_2Cl_2$ was added the hydrochloride salt of the amino acid's methyl ester triethylamine (1.8 mol equiv) followed by 4-hydroxybenzaldehyde (1 mol equiv). The reactions were left stirring for 12 to 16 hours. The $MgSO_4$ was filtered off and the crude product was concentrated under reduced pressure. The crude product was re-dissolved in $CH_2Cl_2$, and washed twice with brine (2×20 ml). The organic solvent was dried over $MgSO_4$ and decolorized with activated carbon. The crude was then purified by flash chromatography in basic alumina or silica treated with triethylamine to give the desired product.

For compound 1, glycine methyl ester hydrochloride (0.4 g, 3.2 mmol) was coupled to 4-hydroxybenzaldehyde (0.4 g, 3.2 mmol, 1 equiv) to give compound 1 (0.28 g, 40%).

$^1$HNMR(270 MHz, $CD_3OD$ ) δ3.74 (3H, s), 4.36 (2H, s), 6.83 (2H, d, J=8.7 Hz), 7.63 (2H, d, J=8.7 Hz), 8.21 (1H, s); MS (ES) m/z 194 (M+H) base peak, 216 (M+Na).

For compound 2a, D-alanine methylester hydrochloride (0.2 g, 1.43mmol) was reacted with 4-hydroxybenzaldehyde (0.175 g, 1.43 mmol), which gave the compound as an off-white solid (0.2 g, 67%).

$^1$HNMR(270 MHz, $CD_3OD$) δ1.46 (3H, d, J=6.4 Hz), 3.72 (3H, s), 4.13 (1H, q, J=6.9 Hz), 6.82 (2H, d, J=8.7 Hz) 7.63 (2H, d, J=8.7 Hz), 8.23 (1H, s); MS (ES) m/z 208 (M+H) base peak, 230 (M+Na).

For compound 2b, L-alanine methylester hydrochloride (0.2 g, 1.43 mmol) was reacted with 4-hydroxybenzaldehyde (0.175 g, 1.43 mmol), which gave compound 2b (0.2 g, 67%).

$^1$HNMR(270 MHz, $CD_3OD$) δ1.46 (3H, d, J=6.4 Hz), 3.72 (3H, s), 4.13 (1H, q, J=6.9 Hz), 6.82 (2H, d, J=8.7 Hz) 7.63 (2H, d, J=8.7 Hz), 8.23 (1H, s); MS (ES) m/z 208 (M+H) base peak, 230 (M+Na).

For compound 3, L-valine methylester hydrochloride (0.4 g, 2.5 mmol) was coupled to 4-hydroxybenzaldehyde (0.3 g, 2.5 mmol) to give compound 3 (0.2 g, 36%).

$^1$HNMR(270 MHz, $CD_3OD$) δ0.87 (3H, d, J=8.1 Hz), 0.94 (3H, d, J=6.9 Hz), 2.23–2.36 (1H, m), 3.63 (1H, d, J=7.7 Hz), 3.73 (3H, s), 6.82 (2H, d, J=8.6 Hz), 7.65 (2H, d, J=8.6 Hz), 8.18 (1H, s); MS (ES) m/z 236 (M+H) base peak, 258 (M+Na).

Compound 4 (0.2 g, 48%), was obtained from L-leucine methyl ester hydrochloride (0.3 g, 1.7 mmol) and 4-hydroxybenzaldehyde (0.2 g, 1.7 mmol).

$^1$HNMR(270 MHz, $CD_3OD$) δ0.91 (3H, d, J=6.4), 0.94 (3H, d, J=6.7 Hz), 1.72–1.81 (2H, m), 3.65–3.70 (1H, m), 3.72 (3H, s), 4.08 (1H, dd, J=7.2, 7.3 Hz), 6.83 (2H, d, J=8.6 Hz), 7.64 (2H, d, J=8.6), 8.23 (1H, s); MS (ES) m/z 250 (M+H) base peak, 272 (M+Na).

For compound 5, L-isoleucine methyl ester hydrochloride (0.3 g, 1.7 mmol) was combined with 4-hydroxybenzaldehyde (0.2 g, 1.7 mmol) to give 5 (0.23 g, 55%).

$^1$HNMR(270 MHz, $CD_3OD$) δ0.85–0.94 (6H, m), 1.17–1.24 (1H, m), 1.44–1.51 (1H, m), 2.01–2.14 (1H, m), 3.72 (3H, s), 3. 73 (1H, d), 6.83 (2H, d, J=8.6 Hz), 7.64 (2H, d, J=8.6), 8.23 (1H, s); MS (ES) m/z 250 (M+H) base peak, 272 (M+Na).

For compound 6, L-methionine methyl ester hydrochloride (0.4 g, 2.0 mmol) and 4-hydroxybenzaldehyde (0.25 g, 2.0 mmol) were combined to give compound 6 (0.23 g, 43%).

$^1$HNMR(270 MHz, $CD_3OD$) δ2.04 (3H, s), 2.04–2.60 (4H, m), 3.73 (3H, s), 4.18 (1H, dd, J=4.9, 8.9Hz), 6.83 (2H, d, J=8.6 Hz), 7.64 (2H, d, J=8.6), 8.24 (1H, s); MS (ES) m/z 268 (M+H) base peak, 290 (M+Na).

For compound 7, L-serine methyl ester hydrochloride (0.4 g, 2.6 mmol) and 4-hydroxybenzaldehyde (0.35 g, 2.6 mmol) were combined to give compound 7 (0.1 g, 20%).

$^1$HNMR(270 MHz, CD$_3$OD) δ3.74 (3H, s), 3.79 (1H, dd, J=11.0, 7.1 Hz), 4.00 (1H, dd, J=4.9, 11.0 Hz), 4.10 (1H, dd, J=7.2, 5.0 Hz), 6.81 (1H, d, J=8.9 Hz), 7.65 (1H, d, J=8.6), 8.23 (1H, s); MS (ES) m/z 224 (M+H), 246 (M+Na) base peak.

EXAMPLE 2

This example provides syntheses of compounds comprising Schiff base condensation products of aromatic amino acids with a benzyaldehyde reactant. To a suspension of anhydrous MgSO$_4$ (0.2 g) and the hydrocloride salt of L-phenylalanine methyl ester (0.3 g, 1.4 mmol) in CH$_2$Cl$_2$ (4.8 mL), triethylamine (0.35 ml, 2.5 mmol) was added followed by 4-hydroxybenzaldehyde (0.17 g, 1.4 mmol). The reaction was left stirring for 24 hrs. The MgSO$_4$ was filtered off and the crude product was concentrated under reduced pressure. The crude product was re-dissolved in a mixture of CH$_2$Cl$_2$/EtOAc, (40/60), and washed twice with brine (2×20 mL). The organic phase was dried over MgSO$_4$ and decolorized with activated carbon. The crude product was then purified by flash chromatography in basic alumina to give the desired product, compound 8 (0.23 g, 58%).

$^1$HNMR(270 MHz, CD$_3$OD) δ3.03 (1H, dd, J=9.1, 13.3 Hz), 3.32 (1H, dd, J=5.2, 13.3 Hz), 3.72 (3H, s), 4.17 (1H, dd, 5.2, 8.9 Hz), 6.78 (2H, d, J=8.6 Hz), 7.16–7.21 (5H, m), 7.52 (2H, d, J=8.7 Hz), 7.8 (1H, s); $^{13}$CNMR(67.5 MHz, CD$_3$OD) δ39.3, 51.3, 73.0, 115.2, 126.3, 128.0, 129.4, 130.3, 165.1, 172.4; MS (ES) m/z 284 (M+H) base peak, 306 (M+Na).

Compound 9 was prepared as above except that a suspension of L-tyrosine methyl ester (0.4 g, 2.1 mmol) was added to a suspension of anhydrous MgSO$_4$ (0.25 g) in CH$_2$Cl$_2$ (4.8 ml) followed by 4-hydroxybenzaldehyde (0.25 g, 2.1 mmol). The reaction was left stirring for 48 hrs. The MgSO$_4$ was filtered off and the crude product was concentrated under reduced pressure to give the desired product compound 9 (0.27 g, 61%).

$^1$HNMR(270 MHz, CD$_3$OD) δ2.92 (1H, dd, J=8.9, 13 Hz), 3.25 (1H, dd), 3.71 (3H, s), 4.10 (1H, dd, J=5.2, 8.9), 6.63 (2H, d, J=8.4 Hz), 6.80 (2H, d, J=8.6 Hz), 9.69 (2H, d, J=8.6 Hz), 7.52 (2H, d, J=8.7 Hz), 7.82 (1H, s); $^{13}$CNMR (67.5 MHz, CD$_3$OD) δ38.6, 51.2, 74.9, 114.7, 115.2, 126.7, 127.9, 130.3, 130.5, 155.8, 160.8, 165.0, 172.7; MS (ES) m/z 299 (M+H), 322 (M+Na), base peak.

For compound 10, the hydrocloride salt of L-tryptophan methyl ester (0.3 g, 1.2 mmol) was added to a suspension of anhydrous MgSO$_4$ (0.2 g) in CH$_2$Cl$_2$ (4.6 m). Triethylamine (0.3 ml, 2.1 mmol) was added, followed by 4-hydroxybenzaldehyde (0.15 g, 1.2 mmol). The reaction was left stirring for 48 hrs. The MgSO$_4$ was filtered off and the crude product was concentrated under reduced pressure. The crude product was re-dissolved in a mixture of CH$_2$Cl$_2$/EtOAc, (40/60), and washed twice with brine (2×20 ml). The organic was dried over MgSO$_4$ and decolorized with activated carbon. The crude product was then purified by flash chromatography in basic alumina to give the desired product compound 10 (0.20 g, 53%).

$^1$HNMR(270 MHz, CD$_3$OD) δ3.12 (1H, dd, J=8.9, 14.4 Hz), 3.50 (1H, dd, J=5.2, 14.4 Hz), 3.73 (3H, s), 4.22 (1H, dd, J=5.2, 8.7 Hz), 6.70–7.54 (9H, m), 7.76 (1H, s); $^{13}$CNMR(67.5 MHz, CD$_3$OD) δ29.3, 51.2, 73.6, 109.8, 110.9, 115.1, 118.0, 118.4, 121.0, 123.6, 127.2, 130.3, 136.7, 164.6, 173.1;MS (ES) m/z 323 (M+H) base peak, 3345 (M+Na).

For compound 8b, triethylamine (0.35 ml, 2.5 mmol) was added followed by 4-hydroxybenzaldehyde (0.17 g, 1.4 mmol) to a suspension of anhydrous MgSO$_4$ (0.2 g) and the hydrocloride salt of D-phenylalanine methyl ester (0.3 g, 1.4 mmol) in CH$_2$Cl$_2$ (4.8 ml). The reaction was left stirring for 24 hrs. The MgSO$_4$ was filtered off and the crude was concentrated under reduced pressure. The crude was then purified by flash chromatography in basic alumina to give the desired product compound 8b (0.32 g, 82%%).

$^1$HNMR(270 MHz, CD$_3$OD) δ3.03 (1H, dd, J=9.1, 13.3 Hz), 3.32 (1H, dd, J=5.2, 13.3 Hz), 3.72 (3H, s), 4.17 (1H, dd, 5.2, 8.9 Hz), 6.78 (2H, d, J=8.6 Hz), 7.16–7,21 (5H, m), 7.52 (2H, d, J=8.7 Hz), 7.8 (1H, s);

For compound 10b, triethylamine (0.3 mL, 2.1 mmol) was added followed by 4-hydroxybenzaldehyde (0.15 g, 1.2 mmol) to a suspension of anhydrous MgSO$_4$ (0.2 g) and the hydrocloride salt of D-tryptophan methyl ester (0.3 g, 1.2 mmol) in CH$_2$Cl$_2$ (4.6 ml). The reaction was left stirring for 48 hrs. The MgSO$_4$ was filtrated off and the crude was then purified by flash chromatography in basic alumina to give the desired product compound 10b (0.28 g, 74%).

$^1$HNMR(270 MHz, CD$_3$OD) δ3.12 (1H, dd, J=8.9, 14.4 Hz), 3.50 (1H, dd, J=5.2, 14.4 Hz), 3.73 (3H, s), 4.22 (1H, dd, J=5.2, 8.7 Hz), 6.70–7.54 (9H, m), 7.76 (1H, s).

EXAMPLE 3

This example provides syntheses of compounds wherein the Schiff base condensation products of protected amino acids with parahydroxybenzaldehyde are reduced. A general synthesis procedure follows the previous procedure except that the purified imine product was suspended in absolute ethanol and NaBH$_4$ (1 mol equiv) was added to each reaction mixture. After 1 hr, the reactions were quenched with water and extracted with CH$_2$Cl$_2$ to give the reduced compounds in quantitative yields once the organic fractions were dried over MgSO$_4$ and evaporated to dryness. Further purification through silica flash chromatography was done.

For compound 11:

$^1$HNMR(270 MHz, CD$_3$OD) δ2.92 (2H, m), 3.45–3.66 (6H, m), 6.69 (2H, d, J=8.4), 6.98–7.30 (7H, m); $^{13}$CNMR (67.5 MHz, CD$_3$OD) δ38.8, 50.8, 50.9, 61.7, 114.8, 126.5, 128.1, 128.9, 129.5, 129.6, 137.1, 156.5, 174.6.

For compound 12:

$^1$HNMR(270 MHz, CD$_3$OD) δ2.87 (2H, m), 3.54–3.62 (6H, m), 6.65–6.74 (4H, m), 6.93 (2H, d, J=8.6 Hz), 7.08 (2H, d, J=8.6 Hz); $^{13}$CNMR(67.5 MHz, CD$_3$OD) d 37.4, 50.8, 51.1, 61.6, 115.0, 126.8, 127.8, 129.9, 156.2, 156.9, 173.5

For compound 13:

$^1$HNMR(270 MHz, CD$_3$OD) δ3.11 (2H, m), 3.45–3.65 (6H, m), 6.50–7.42 (7H, m); $^{13}$CNMR(67.5 MHz, CD$_3$OD) δ28.6, 50.9, 51.0, 60.8, 109.4, 111.0, 114.8, 117.9, 118.4, 121.1, 123.1, 127.3, 129.5, 136.7, 156.4, 174.9.

EXAMPLE 4

This example provides syntheses of compounds comprising condensation products of protected amino acids with benzaldehyde. For compound 14, the same general procedure was followed as for compound 8 to give compound 14 (0.2 g, 61%).

$^1$HNMR(270 MHz, CD$_3$OD) δ3.05 (1H, dd, J=9.1, 13.6 Hz), 3.24 (1H, dd, J=4.8, 13.6 Hz), 3.73 (3H, s), 4.24 (1H, dd, J=4.9, 9.1 Hz), 7.13–7.19 (4H, m), 7.30–7.50 (3H, m), 7.66 (2H, m), 7.96 (1H, s).

For compound 15, the same general procedure was followed as for compound 9 to obtain 15 (0.4 g, 90%).

¹HNMR(270 MHz, CD$_3$OD) δ2.94 (1H, dd, J=8.9, 13.9 Hz), 3.24 (1H, dd, J=4.9, 13.9), 3.73 (3H, s), 4.16 (1H, dd, J=4.9, 8.9), 6.61 (2H, d, J=8.6 Hz), 6.96 (2H, d, J=8.4), 7.38–7.50 (3H, m) 7.64–7.70 (2H, m), 7.94 (1H, s).

For compound 16, the same general procedure was followed as for compound 10 to give compound 16 (0.16 g, 46%).

¹HNMR(270 MHz, CD$_3$OD) δ3.15 (1H, dd, J=8.9, 14 Hz), 3.49 (1H, dd, J=4.7, 14 Hz), 3.73 (3H, s), 4.28 (1H, dd, J=4.7, 8.4 Hz), 6.92–7.63 (10H, m), 7.82 (1H, s).

EXAMPLE 5

This example provides syntheses of compounds that feature differently substituted benzaldehyde moieties. A general synthesis provides that a benzaldehyde with the appropriate substituent/s was added (1 mol equiv) to a suspension in CH$_2$Cl$_2$ of anhydrous MgSO$_4$ and L-tyrosine methyl ester. The reaction was left stirring for 48 hrs. The MgSO$_4$ was filtered off and the crude product was concentrated under reduced pressure to give the desired product.

Compound 17 was obtained (0.42 g, 91%).

¹HNMR(270 MHz, CD$_3$OD) δ2.93 (1H, dd, J=8.9, 13.6 Hz), 3.23 (1H, dd, J=4.9, 13.4 Hz), 3.72 (3H, s), 4.13 (1H, dd, J=4.9, 8.9 Hz), 6.61–7.28 (8H, m) 7.85 (1H, s).

Compound 18 was obtained pure (0.38 g, 82%).

¹HNMR(270 MHz, CD$_3$OD) δ2.97 (1H, dd, J=8.9, 13.6 Hz), 3.23 (1H, dd, J=4.9, 13.4 Hz), 3.73 (3H, s), 4.21 (1H, dd, J=4.9, 8.7 Hz), 6.62–7.34 (8H, m) 8.06 (1H, s).

Compound 19 was obtained pure (0.38 g, 75%).

¹HNMR(270 MHz, CD$_3$OD) δ2.97 (1H, dd, J=8.9, 13.3 Hz), 3.26 (1H, dd, J=4.7, 13.9 Hz), 3.73 (3H, s), 4.25 (1H, dd, J=4.7, 8.9 Hz), 6.62 (2H, d, J=8.4 Hz), 6.94 (2H, d, J=8.6 Hz), 7.91 (2H, d, J=8.9 Hz), 8.03 (1H, s), 8.26 (2H, d, J=8.9 Hz).

Compound 20 was obtained (0.47 g, 98%).

¹HNMR(270 MHz, CD$_3$OD) δ2.28 (1H, dd, J=8.6, 13.6 Hz), 3.24 (1H, dd, J=8.9, 13.6 Hz), 3.73 (3H, s), 4.23 (1H, dd), 6.61–69.8 (7H, m), 8.02 (1H, s).

Compound 21 was obtained (0.41 g, 85%).

¹HNMR(270 MHz, CD$_3$OD) δ2.91 (1H, dd, J=8.9, 13.6 Hz), 3.20 (1H, dd, J=5.2, 13.8 Hz), 3.71 (3H, s), 4.09 (1H, dd, J=4.5, 9.3 Hz), 6.61–6.98 (6H, m), 7.18 (1H, s), 7.74 (1H, s).

EXAMPLE 6

This example provides syntheses of compounds that feature differently substituted benzaldehyde moieties. A general synthesis provides that a benzaldehyde with the appropriate substituent was added (1 mol equiv) to a suspension in CH$_2$Cl$_2$ of anhydrous MgSO$_4$ and L-tyrosine methyl ester. The reaction was left stirring for 48 hrs. The MgSO$_4$ was filtered off and the crude product was concentrated under reduced pressure to give the desired product.

After condensation, compound 22 was obtained (0.38 g, 78%).

¹HNMR(270 MHz, CD$_3$OD) δ2.92 (1H, dd, J=8.9, 13.4 Hz), 3.20 (1H, dd, J=4.9, 13.6 Hz), 3.70 (3H, s), 4.14 (1H, dd, J=4.9, 8.9 Hz), 6.64 (2H, d, J=8.4 Hz), 6.94 (2H, d, J=8.4), 7.37 (2H, d, J=8.6 Hz), 7.62 (2H, d, J=8.4), 7.87 (1H, s).

After condensation, compound 23 was obtained (0.29 g, 52%).

¹HNMR(270 MHz, CD$_3$OD) δ2.95 (1H, dd, J=4.5, 13.6 Hz), 3.22 (1H, dd, J=5.2, 13.6 Hz), 3.70 (3H, s), 4.15 (1H, dd, J=4.9, 8.9 Hz), 6.63 (2H, d, J=8.4), 6.94 (2H, d, J=8.6), 7.55 (4H, s), 7.86 (1H, s).

Compound 24 was obtained following the general procedure (0.12 g, 25%).

¹HNMR(270 MHz, CD$_3$OD) δ2.92 (1H, dd, J=9.1, 13.6 Hz), 3.22 (1H, dd, J=5.2, 13.6 Hz), 3.70 (3H, s), 4.16 (1H, dd, J=5.2, 9.2 Hz), 6.63 (2H, d, J=8.6 Hz), 6.95 (2H, d, J=8.7 Hz), 7.11–7.18 (2H, m), 7.70–7.73 (2H, m), 7.92 (1H, s). ¹³CNMR (67.5 MHz, CD$_3$OD) δ38.6, 50.0, 74.8, 114.7, 115.2, 115.5, 127.7, 130.5, 135.6, 155.9, 163.6, 172.5.

Compound 25 was obtained following the general procedure (0.23 g, 51%).

¹HNMR(270 MHz, CD$_3$OD) δ2.35 (3H, s), 2.94 (1H, dd, J=9.2, 13.6 Hz), 3.24 (1H, dd, J=5.2 13.6 Hz), 3.71 (3H, s), 4.13 (1H, dd, J=5.2, 8.9 Hz), 6.63 (2H, dd, J=8.4 Hz), 6.95 (2H, dd, J=8.7 Hz), 7.21 (2H, d, J=7.9 Hz), 7.56 (2H, d, J=8.2 Hz), 7.88 (1H, s).

Compound 26 exemplifies a further type of compound in which the protecting group of the amino acid moiety is tert butyl. 4-hydroxybenzaldehyde (0.26 g, 2.1 mmol) was added to a suspension in CH$_2$Cl$_2$ (7 ml) of anhydrous MgSO$_4$ (0.35 g) and L-tyrosine t-butyl ester (0.5 g, 2.1 mmol). The reaction was left stirring for 48 hrs. The MgSO$_4$ was filtered off and the crude was concentrated under reduced pressure to give the desired product compound 26 (0.29 g, 49%).

¹HNMR(270 MHz, CD$_3$OD) δ1.39 (9H, s), 3.14 (1H, dd, J=8.6, 13.4 Hz), 3.16 (1H, dd, J=5.9, 4.7 Hz), 3.34 (3H, s) 3.99 (1H, dd), 6.64 (2H, d, J=8.7), 6.80 (2H, d, J=8.7 Hz), 6.98 (2H, d, J=8.6 Hz), 7.55 (2H, d, J=8.6), 7.87 (1H, s).

EXAMPLE 7

This example provides syntheses of further compounds that comprise a halo-substituted benzaldehyde moiety. A general synthesis provides that triethylamine (1.8 mol equiv) and the desired halo-substituted parabenzaldehyde (1 mol equiv) were added to a preparation of the hydrochloride salt of L-tryptophan methyl ester in a suspension of anhydrous MgSO$_4$ in CH$_2$Cl$_2$. The reactions were left stirring for 24hrs. The MgSO$_4$ was filtered off and the crude product was concentrated under reduced pressure. The crude product was then purified by flash chromatography in basic alumina to give the desired product.

Compound 27 was obtained following the general procedure (0.17 g, 42%).

¹HNMR(270 MHz, CD$_3$OD) δ3.13 (1H, dd, J=8.9, 14.3 Hz), 3.45 (1H, dd, J=4.7, 14.3 Hz), 3.67 (3H, s), 4.21 (1H, dd, J=4.7, 8.9 Hz) 6.80–7.54 (9H, m), 7.65 (1H,s).

Compound 28 was obtained following the general procedure (0.22 g, 48%).

¹HNMR(270 MHz, CD$_3$OD) δ3.16 (1H, dd, J=8.9, 14.6 Hz) 3.48 (1H, dd, J=5.2, 14.6 Hz), 3.74 (3H, s), 4.29 (1H, dd, J=5.2, 8.9 Hz), 6.94–7.08 (4H, m), 7.28 (1H, d, J=7.7 Hz), 7.54 (4H, s), 7.81 (1H, s).

After condensation, compound 29 was obtained (0.22 g, 58%).

¹HNMR(270 MHz, CD$_3$OD) δ3.15 (1H, dd, J=8.9, 14.3 Hz), 3.51 (1H, dd, J=4.9, 14.3 Hz), 3.7 (1H, dd), 4.24 (1H, dd, J=4.9, 8.9 Hz), 6.80–7.64 (9H, m), 7.75 (1H, s).

EXAMPLE 8

Schiff base conjugation products, especially conjugated imines, are of moderate stability. Although lability has not been problematic with the amino acid/benzaldehyde Schiff base (AA/BSB) compounds of the present invention, Schiff base condensation products can hydrolyze to yield the original free amine and aldehyde reactants. Compounds of the present invention, having an imine bond between the amino acid and the benzaldehyde moieties, showed greater potency as inhibitors of MIF activity than did corresponding compounds wherein the imine bond was specifically reduced, suggesting that unsaturation at this linkage is a relevant feature. Since carba analogs of the Schiff base condensation products can be expected to exhibit increased stability relative to their imine counterparts, carba analogs of the AA/BSB's can be prepared and evaluated. For example, the imine bond (carbon-nitrogen double bond) of the above exemplified compounds can be substituted by a carbon-carbon double bond or by a carbon-carbon triple bond providing, respectively, 2-substituted-4-phenyl-but-3-enoic and 2-substituted-4-phenyl-but-3-ynoic acids and methyl esters thereof as carba analogs of amino acid/benzaldehyde Schiff base condensation products described in detail above.

As a general approach, L- and D-amino acids are utilized as a starting point. L- D-aromatic amino acids, for instance, are transformed to R and S-2-bromo-propionic acid, respectively, as described previously (Olah et al., *Helvetica Chimica Acta* 66:1028–1030, 1983; Cushman et al., *Biochemistry* 16:5484–5491, 1977). The aromatic L-amino acids phenylalanine, tyrosine or tryptophan, for instance, are individually dissolved in 47% hydrobromic acid in water and then treated with sodium nitrite at 0° C. The reaction stirs for two hours at the same temperature and the product is extracted in ethyl ether. This method delivers the bromo derivative of each individual amino acid in moderate to high yield (45–88%). Next, the nucleophilic substitution of the bromo by the phenylacetylenic carbanion lithium salt produces the first desired compounds, namely the acetylenic derivatives (Inhardt and Fried, *Synthesis* 4, 285–291, 1990). Phenylacetylene is commercially available and the other substituted phenylacetylenes are prepared via Heck reaction. For instance, 4-Iodophenol is subjected to palladium-catalyzed substitution with ethynyltrimethylsilane followed by the removal of trimethylsilyl group using refluxing methanolic KOH to form 4-hydroxyphenylacetylene (Sonogashira et al., *Tetrahedron Letters* 16:4467–4470, 1975; Tischler and Lanza, *Tetrahedron Letters* 27:1653–1656, 1986).

These acetylenic carba analogs are conveniently reduced to provide the desired olefinic carba analogs. Acetylenic bond reduction is well established and is of particular interest because specific reduction conditions can be employed to selectively generate the Z- or the E-geometric isomers. Using Lindlar catalyst (Pd—CaCO$_3$—PbO) in ethanol and one atomosphere of hydrogen, for instance, yields the Z-alkene with little or no Z-E isomerization (Denmark and Jones, *J. Org. Chem.* 47:4595–4597, 1982). The E-isomer is obtained by metal reduction, for instance Na in NH$_3$ or lithium aluminum hydride. Moreover, it has been found that Red-A1 (NaAlH$_2$(OCH$_2$CH$_2$CH$_2$OMe)$_2$) is the fastest, highest yielding and more stereo-selective reduction among the metal hydrides examined (Brandsma et al., *Eur. J. Org. Chem.* 4:775–779, 1999; Schreiber et al., *J. Amer. Chem. Soc.* 109:1525–1529, 1987), such that this is a suitable reducing reagent to arrive at the E-isomer.

It is particularly noteworthy that specific interaction of the acetylenic derivatives with MIF results in allene formation. Most likely, this reflects carbanion generation via abstraction of the alpha-proton by a basicity within the MIF active site, followed by rearrangement to a conjugated allene. Consequently, after some turnover, the active site proline-1 residue of MIF captures the allene molecule alkylatively, leading to an enzymatically inactive protein (Jung et al., *Biochemistry* 17:2628–2632, 1978) with a corresponding loss of MIF biological activity.

Alternatively, synthesis of 2-benzyl-4(4-hydroxyphenyl)-but-3-enoic acid methyl ester (the carba analog of phenylalanine/para-hydroxybenzaldehyde Schiff base, compound 30) is accomplished according to a general approach involving Heck's reaction, as illustrated by Scheme 1:

Scheme 1: Synthesis of the carba analog of phenylalanine/p-hydroxybenzaldehyde Schiff base (compound 30)

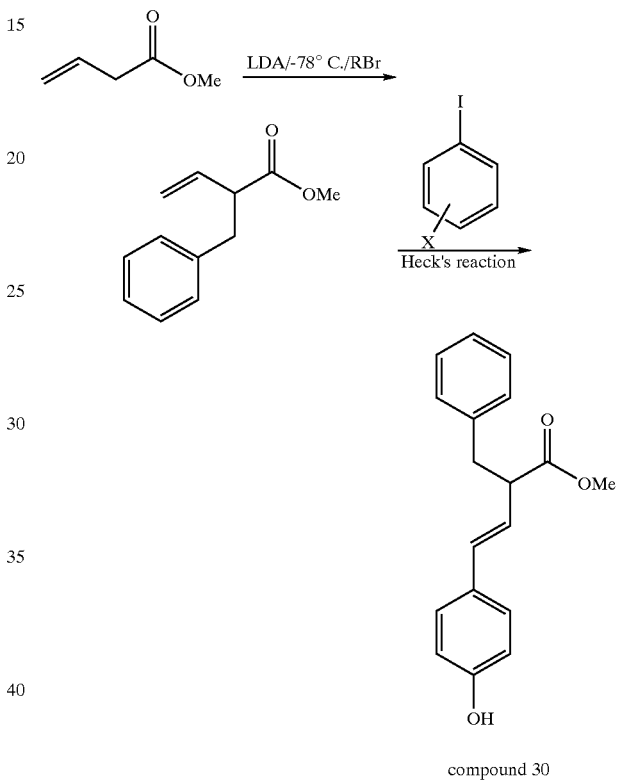

compound 30

In this specific example, methyl-3-butenoate (0.53 mL, 5 mmol) is syringed into a THF (20 mL) solution of lithium diisopropylamine (LDA; 5 mmol) at −78° C. After 30 minutes, benzyl bromide (0.4 mL, 3.3 mmol) dissolved in THF (1.5 mL) is added dropwise and the reaction mixture is warmed up to −30° C. The reaction is allowed to proceed for 2 hrs and then quenched by adding aqueous ammonium chloride. After the reaction mixture warms to room temperature, it is extracted with ether (3×20 mL) and the organic phase is dried over magnesium sulfate. After flash chromatography, the olefinic compound is obtained in 82% yield (0.52 g). Coupling with p-iodophenol under Heck's reaction conditions furnishes quantitatively the desired compound 30. This synthetic approach is easily generalized to provide additional carba analogs of amino acid/(optionally substituted)benzaldehyde Schiff base antagonists of MIF of the present invention according to Formula I by: (i) varying the RBr reagent (above) to provide side chain functionalities corresponding to the amino acid component of the MIF antagonists of Formula I; and/or (ii) varying the iodophenol reagent (above) to provide variously derived benzaldehyde components of the MIF antagonists of Formula I.

EXAMPLE 9

This example provides comparative pharmacologic activity data of the foregoing compounds. As described in detail above (see particularly in the Detailed Description) an assay for MIF tautomerase activity that is predictive of biological MIF inhibitory activity in vivo was used to evaluate the test compounds and identify those predicted to have MIF inhibitory activity. Briefly, the assay procedure involves measuring MIF tautomerase activity in the presence of test compound (potential inhibitors) using an L-dopachrome methyl ester as substrate. Various concentrations of inhibitor compounds were added and an $IC_{50}$ determined for enzyme (tautomerase) inhibitory activity. These $IC_{50}$ values, together with other indices of inhibitory activity (for example, percent inhibition at 100 μM of test compound) are reported in connection with the structural diagrams of the test compounds in the Detailed Description. Compounds are additionally assessed for inhibition of MIF biological activities in any of a number of assays for MIF activity including, for example, inhibition of MIF binding to target cells, inhibition of MIF release or synthesis, inhibition of MIF immunoreactivity with MIF-specific antibodies, alterations of MIF conformation or structural integrity as assessed by circular dichroism spectroscopy or thermal stability measurement, inhibition of the pro-proliferative effects of MIF on quiescent NIH/3T3 cells and inhibition of the associated prolonged ERK activation therein, inhibition of MIF-induced arachadonic acid release from NIH/3T3 cells, inhibition of MIF-induced fructose 2,6 bisphosphate formation in L6 myocytes, inhibition of MIF toxicity in TNF or LPS-challenged test animals, inhibition of the glucocorticoid counter-regulatory activity of MIF in vitro or in vivo, and inhibition of morbidity or mortality in any of a number of animal models of human diseases that are characterized by the release, production and/or appearance of MIF. The activity of MIF antagonists may also be assessed in various well-known and accepted in vitro and in vivo models of cancer, including particularly tumor cell proliferation assays, tumor cell killing assays, solid tumor growth and/or metastasis assays, and in various known and accepted in vitro and in vivo models of angiogenesis or neovascularization including, for example, endothelial cell proliferation and differentialtion assays, Matrigel™ assays, angiogenesis and tumor angiogenesis assays, and the like.

Compounds 10 (corresponding to L-TrpME/parahydroxybenzaldehyde Schiff base) and 9 (corresponding to L-TyrME/parahydroxybenzaldehyde Schiff base) exhibited MIF inhibitory activity in a representative assay for MIF biological activity (i.e., inhibition of MIF induced proliferation in quiescent NIH/3T3 cell cultures) and inhibited enzymatic activity with $IC_{50}$ values of about 5 μM and 10 μM, respectively. Neither compound 8 (corresponding to L-PheME/parahydroxybenzaldehyde Schiff base) nor compound 10b (corresponding to D-TrpME/parahydroxybenzaldehyde Schiff base) exhibited anti-MIF biological activity (NIH/3T3 cell proliferation assay) and these compounds exhibited $IC_{50}$ values for MIF tautomerase inhibition of about 50 μM and 100 μM, respectively. The activity of compound 10 is further exemplified by reference to FIG. 1, which summarizes experimental results showing that compound 10 is as effective an MIF antagonist as a neutralizing anti-MIF monoclonal antibody (mAb). In the illustrative experiments, briefly, DME medium (supplemented with 10% serum) was added to quiescent NIH/3T3 fibroblasts together with a neutralizing anti-MIF mAb, or L-tryptophan/para-hydroxybenzaldehyde Schiff base (i.e., compound 10) or D-tryptophan/para-hydroxybenzaldehyde Schiff base (i.e., compound 10b). Proliferation was assessed by the incorporation of [3H]-thymidine into DNA and % suppression of proliferation was calculated. The results shown are the mean of duplicate assays and are representative of two separate experiments. Therefore, these data show a correlation between inhibition of MIF tautomerase activity and anti-MIF biological activity.

Figure 2:
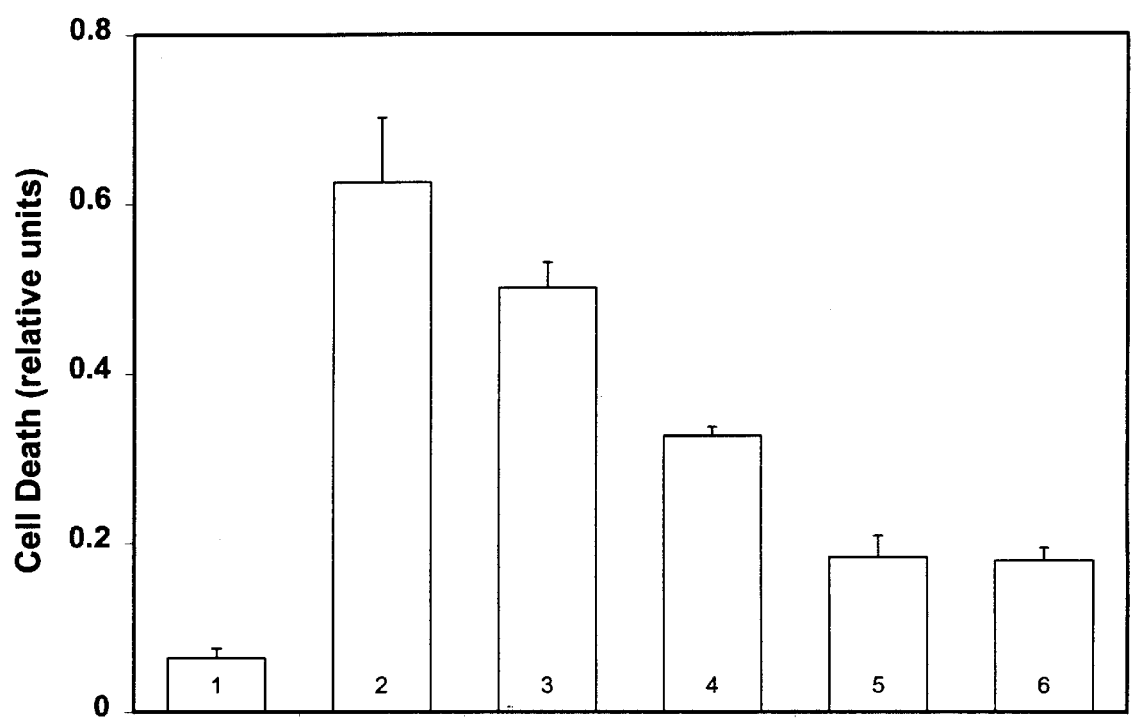
FIG. 2 compares the activity of MIF antagonist agents of the present invention (and more particularly compounds according to Formula I) to neutralize the MIF-mediated protection from apoptosis induced in cultured murine embryonic fibroblasts, which apoptotic response (cell death) is initiated by withdrawal of serum. In this assay, withdrawal of serum initiates an apoptotic response, but the cells can be rescued by addition of recombinant MIF (rMIF) to the culture medium. Treatment with MIF antagonist compound 10 (L-tryptophan/para-hydroxybenzaldehyde Schiff base), but not compound 10b (D-tryptophan/para-hydroxybenzaldehyde Schiff base), was as effective as a monoclonal anit-MIF antibody treatment at neutralizing rMIF added to the cultures, as evidenced by persistence of apoptosis despite addition of rMIF in cultures treated with compound 10. Note the dose-related effect of treatment. This antagonistic effect on MIF bioactivity in vitro is predictive of clinical utility of the active MIF antagonist agent.

The activity of compound 10 as an MIF antagonist is still further exemplified by reference to FIG. 2, which summarizes experimental results showing that compound 10 is as effective an MIF antagonist agent as is a neutralizing anti-MIF monoclonal antibody (mAb). The following table correlates the experimental conditions with the bar graph shown in FIG. 2.

| Bar # | Experimental condition |
|---|---|
| 1 | + serum |
| 2 | + serum-free |
| 3 | + serum-free + rMIF + L-trp/SB at 10 μM (compound 10) |
| 4 | + serum-free + rMIF + L-trp/SB at 1 μM (compound 10) |
| 5 | + serum-free + rMIF + D-trp/SB at 10 μM (compound 10b) |
| 6 | + serum-free + rMIF |

In the illustrative experiments, cultured embryonic fibroblasts are induced to enter apoptosis (cell death) as a result of serum withdrawal. These cultures can be "rescued" by treatment with MIF. Thus, test compounds are conveniently assayed for MIF antagonist activity by reference to the activity of the compounds to neutralize the effect of added MIF in the apoptosis assay; that is, by the persistence of apoptosis (cell death) in serum-free culture conditions despite the addition of MIF. In this regard, anti-MIF antibodies are known to antagonize MIF and serve as a convenient positive control.

Briefly, primary murine embryonic fibroblasts are distributed into 6-well cell culture plates at $2 \times 10^5$ cells/well. Cells are subsequently cultured overnight under standard conditions in 10% serum-containing medium (+serum) or in serum-free medium (+serum-free) in the absence or presence of recombinant human MIF (rMIF) at 50 ng/ml. Test compound vehicle alone ($Me_2SO$) or Schiff base-type MIF antagonist test compounds (L-trp/SB=L-tryptophan/para-hydroxybenzaldehyde Schiff base, compound 10; D-trp/SB =D-tryptophan/para-hydroxybenzaldehyde Schiff base, compound 10b) dissolved in vehicle are preincubated with rMIF in serum-free medium for five minutes prior to addition to cell cultures. Cell lysates are analyzed for apoptosis by any of a variety of convenient methods, such as ELISA for fragmented DNA. Results shown are the mean+/−SD of duplicate samples and are representative of replicated experiments. At a dose of 10 μM, compound 10 significantly antagonizes the bioactivity of MIF in this in vitro assay that is predictive of clinical utility for conditions, diseases, or indications wherein MIF is released from cellular stores and/or MIF synthesis or appearance is increased.

We claim:

1. A compound of the following formula:

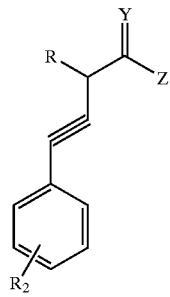

wherein Y is O, C(R$_1$)$_2$, or S;

wherein Z is OH, R$_1$, —CH$_2$—N(R$_1$)$_2$, or SR$_1$;

wherein R$_1$ is independently H, straight or branched C$_1$–C$_6$ alkyl straight or branched C$_2$–C$_6$ alkenyl, or when R$_1$ is attached to a carbon atom, straight or branched C$_1$–C$_6$ alkoxy;

wherein R$_2$ is a single or multiple substitution independently H, OH, R$_1$, N(R$_1$)$_2$, SR$_1$ or a halogen; and wherein R is the side-chain of any naturally occurring alpha amino acid;

and pharmaceutically acceptable salts thereof.

2. A compound of a formula selected from the following group:

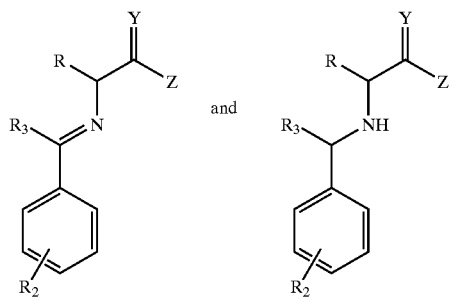

wherein Y is O, C(R$_1$)$_2$, or S;

wherein Z is R$_1$, —CH$_2$—N(R$_1$)$_2$, or SR$_1$;

wherein R$_1$ is independently H, straight or branched C$_1$–C$_6$ alkyl, straight or branched C$_2$–C$_6$ alkenyl, or when R$_1$ is attached to a carbon atom, straight or branched C$_1$–C$_6$ alkoxy;

wherein R$_2$ is a single or multiple substitution independently H, OH, R$_1$, N(R$_1$)$_2$, SR$_1$ or a halogen;

wherein R$_3$ is H, R$_1$, or a halogen;

wherein R is the side-chain of any naturally occurring alpha amino acid;

and pharmaceutically acceptable salts thereof, and wherein in the latter of the two above formulae, when Y is O and Z is OMe, R$_3$ and R$_2$ are not both H.

3. The compound of claim 2, wherein Y is O and Z is OMe.

4. The compound of claim 2, wherein R$_2$ is OH, and R$_3$ is H.

5. The compound of claim 4, wherein R$_2$ is in a para position.

6. The compound of claim 2, which is a compound of Formula II:

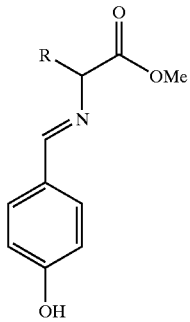

wherein R is selected from the group consisting of: H; —CH$_3$; —CH(CH$_3$)$_2$; —CR$_2$CH(CH$_3$)$_2$; —CH(CH$_3$)CH$_2$CH$_3$; —CH$_2$CH$_2$SCH$_3$; and —CH$_2$OH.

7. The compound of claim 2, wherein R is the side-chain of an aromatic alpha amino acid, Y is O, and Z is OMe such that together the nitrogen atom, Y, Z and R form a protected L aromatic amino acid moiety.

8. The compound of claim 7, wherein R$_2$ is OH, and R$_3$ is H.

9. The compound of claim 7, wherein R is selected from the group consisting of: —CH$_2$-phenyl, —CH$_2$-para-hydroxyphenyl, and —CH$_2$-indoyl.

10. A pharmaceutical composition comprising a compound of a formula selected from the following group:

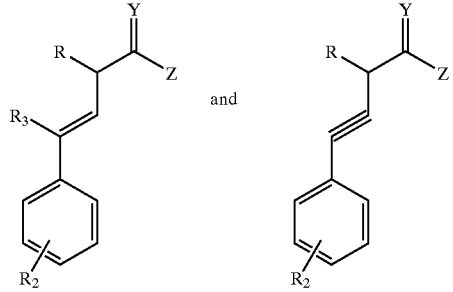

wherein Y is O, C(R$_1$)$_2$, or S;

wherein Z is OH, R$_1$, —CH$_2$—N(R$_1$)$_2$, or SR$_1$;

wherein R$_1$ is independently H, straight or branched C$_1$–C$_6$ alkyl, straight or branched C$_2$–C$_6$ alkenyl, or when R$_1$ is attached to a carbon atom, straight or branched C$_1$–C$_6$ alkoxy;

wherein R$_2$ is a single or multiple substitution independently H, OH, R$_1$, N(R$_1$)$_2$, SR$_1$ or a halogen;

wherein R$_3$ is H, R$_1$, or a halogen;

wherein R is the side-chain of any naturally occurring alpha amino acid;

or a pharmaceutically acceptable salt thereof, together with a pharmaceutically acceptable carrier or diluant.

11. A pharmaceutical composition comprising a compound of claim 2 or a pharmaceutically acceptable salt thereof, together with a pharmaceutically acceptable carrier or diluant.

12. A method for treating cancer or immune, autoimmune, or inflammatory disorders including arthritis, proliferative vascular disease, ARDS (acute respiratory distress syndrome), cytokine-mediated toxicity, sepsis, septic shock, psoriasis, interleukin-2 toxicity, asthma, MIF-mediated conditions, rheumatoid arthritis, insulin dependent diabetes, multiple sclerosis, graft versus host disease, lupus syndromes, and conditions characterized by local or systemic MIF release or synthesis, comprising administering an effective amount of a compound or a pharmaceutically acceptable salt thereof, or a combination of compounds or of pharmaceutically acceptable salts thereof, of a formula selected from the following group:

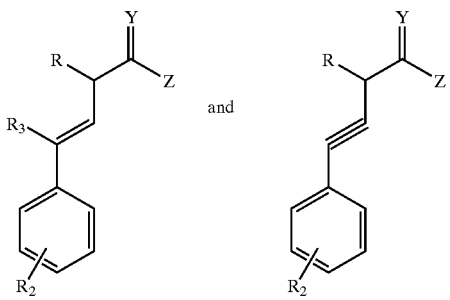

wherein Y is O, C(R$_1$)$_2$, or S;
wherein Z is OH, R$_1$, —CH$_2$—N(R$_1$)$_2$, or SR$_1$;
wherein R$_1$ is independently H, straight or branched C$_1$–C$_6$ alkyl, straight or branched C$_2$–C$_6$ alkenyl, or when R$_1$ is attached to a carbon atom, straight or branched C$_1$–C$_6$ alkoxy;
wherein R$_2$ is a single or multiple substitution independently H, OH, R$_1$, N(R$_1$)$_2$, SR$_1$ or a halogen;
wherein R$_3$ is H, R$_1$, or a halogen;
wherein R is the side-chain of any naturally occurring alpha amino acid.

13. A method for treating cancer or immune, autoimmune, or inflammatory disorders including arthritis, proliferative vascular disease, ARDS (acute respiratory distress syndrome), cytokine-mediated toxicity, sepsis, septic shock, psoriasis, interleukin-2 toxicity, asthma, MIF-mediated conditions, rheumatoid arthritis, insulin dependent diabetes, multiple sclerosis, graft versus host disease, lupus syndromes, and conditions characterized by local or systemic MIF release or synthesis, comprising administering an effective amount of a compound or a pharmaceutically acceptable salt thereof, or a combination of compounds or of pharmaceutically acceptable salts thereof, of claim 2.

14. A method for treating a disorder or disease condition characterized by undesired MIF activity comprising administration of a compound or pharmaceutically acceptable salt thereof of a formula selected from the following group:

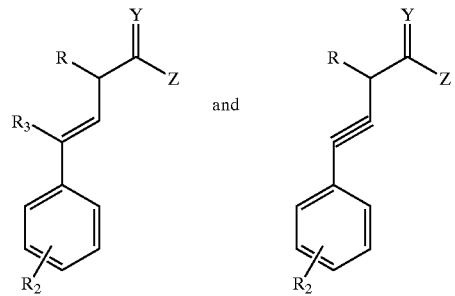

wherein Y is O, C(R$_1$)$_2$, or S;
wherein Z is OH, R$_1$, —CH$_2$—N(R$_1$)$_2$, or SR$_1$;
wherein R$_1$ is independently H, straight or branched C$_1$–C$_6$ alkyl, straight or branched C$_2$–C$_6$ alkenyl, or when R$_1$ is attached to a carbon atom, straight or branched C$_1$–C$_6$ alkoxy;
wherein R$_2$ is a single or multiple substitution independently H, OH, R$_1$, N(R$_1$)$_2$, SR$_1$ or a halogen;
wherein R$_3$ is H, R$_1$, or a halogen;
wherein R is the side-chain of any naturally occurring alpha amino acid, in conjunction with at least one steroidal or non-steroidal anti-inflammatory agent.

15. A method for treating a disorder or disease condition characterized by undesired MEF activity comprising administration of a compound or pharmaceutically acceptable salt thereof of claim 2 in conjunction with at least one steroidal or non-steroidal anti-inflammatory agent.

* * * * *